US010265545B2

(12) United States Patent
Galyaev

(10) Patent No.: US 10,265,545 B2
(45) Date of Patent: Apr. 23, 2019

(54) IONIZING PARTICLE BEAM FLUENCE AND POSITION DETECTOR ARRAY USING MICROMEGAS TECHNOLOGY WITH MULTI-COORDINATE READOUT

(71) Applicant: Radiation Detection and Imaging Technologies, LLC, Phoenix, AZ (US)

(72) Inventor: Evgeny Galyaev, Salt Lake City, UT (US)

(73) Assignee: RADIATION DETECTION AND IMAGING TECHNOLOGIES, LLC, Phoenix, AZ (US)

( * ) Notice: Subject to any disclaimer, the term of this patent is extended or adjusted under 35 U.S.C. 154(b) by 0 days.

(21) Appl. No.: 15/589,883

(22) Filed: May 8, 2017

(65) Prior Publication Data

US 2017/0319872 A1 Nov. 9, 2017

Related U.S. Application Data

(60) Provisional application No. 62/332,882, filed on May 6, 2016.

(51) Int. Cl.
*A61N 5/10* (2006.01)
*H01J 37/244* (2006.01)
*H01J 37/08* (2006.01)

(52) U.S. Cl.
CPC ......... *A61N 5/1049* (2013.01); *A61N 5/1048* (2013.01); *A61N 5/1065* (2013.01);
(Continued)

(58) Field of Classification Search
USPC ...................................................... 250/492.3
See application file for complete search history.

(56) References Cited

U.S. PATENT DOCUMENTS

| 5,347,130 A | * | 9/1994 | Berthold | ................. G01T 1/185 |
| | | | | 250/374 |
| 5,686,721 A | | 11/1997 | Schmidt-Bocking | |

(Continued)

FOREIGN PATENT DOCUMENTS

WO     2013029748     5/2013

OTHER PUBLICATIONS

Charpak, Georges, Multiwire and drift proportional chambers, Physics Today, Oct. 1978, pp. 23-30.
(Continued)

*Primary Examiner* — Phillip A Johnston
(74) *Attorney, Agent, or Firm* — Booth Udall Fuller, PLC

(57) ABSTRACT

A particle beam detector system can comprise a particle beam generator, a particle beam fluence and position detector array based on Micromegas technology, and data readout electronics coupled to the position detector array. The particle beam fluence and position detector array can comprise a sealed, gas-filled, ionizing radiation detector chamber. A printed circuit board (PCB) can be disposed within the ionizing radiation detector chamber, the PCB comprising a multi-layer array arrangement of interconnected conductive sensor pads comprising three planar coordinate grids, X, Y, and ST (stereo) situated on separate layers of the PCB. The multi-layer array arrangement of interconnected conductive sensor pads can comprise a first footprint. A dielectric lattice structure can be disposed over the PCB and the multi-layer array arrangement of sensors. A conductive mesh structure can comprise a second footprint disposed over the dielectric lattice structure and extending over an entire area of the first footprint.

21 Claims, 13 Drawing Sheets

(52) U.S. Cl.
CPC ......... *A61N 5/1075* (2013.01); *A61N 5/1077* (2013.01); *H01J 37/08* (2013.01); *H01J 37/244* (2013.01); *A61N 2005/1087* (2013.01)

(56) References Cited

U.S. PATENT DOCUMENTS

| | | | | |
|---|---|---|---|---|
| 6,011,265 | A * | 1/2000 | Sauli | H01J 47/02 250/374 |
| 6,133,575 | A * | 10/2000 | Charpak | G01T 1/185 250/374 |
| 6,950,492 | B2 * | 9/2005 | Besson | A61B 6/032 378/16 |
| 7,518,117 | B2 * | 4/2009 | Bryman | G01T 1/1603 250/370.1 |
| 8,552,731 | B2 * | 10/2013 | Nichiporov | A61N 5/1048 324/464 |
| 8,853,643 | B2 * | 10/2014 | De Oliveira | G01T 1/185 250/374 |
| 2004/0007670 | A1 | 1/2004 | Bryman | |
| 2008/0029709 | A1 | 2/2008 | Yeo | |
| 2010/0108901 | A1 | 5/2010 | Prieels et al. | |
| 2010/0265078 | A1 | 10/2010 | Friedman | |
| 2011/0248188 | A1 | 10/2011 | Brusasco et al. | |
| 2011/0284757 | A1 | 11/2011 | Butuceanu et al. | |
| 2012/0264064 | A1 | 10/2012 | Giomataris et al. | |
| 2014/0239185 | A1 | 8/2014 | de Oliveira et al. | |
| 2015/0041665 | A1 | 2/2015 | Hollebeek et al. | |
| 2016/0377522 | A1 | 12/2016 | Aune | |

OTHER PUBLICATIONS

Giomataris, I. et al, Micromegas: a high-granularity position-sensitive gaseous detector for high particle-flux environments, Nuclear Instruments and Methods in Physics Research A 376, Jan. 1976, pp. 29-35.

Babichev, E.A. et al, Digital radiographic scanning installation with multiwire proportional chamber, Nuclear Instruments and Methods in Physics Research A310, 1991, pp. 449-454.

Byszewski M. et al, Resistive-strips micromegas detectors with two-dimensional readout, 2nd International Conference on Micro Pattern Gaseous Detectors, 2012, pp. 1-7.

Peskov, V. et al, Advances in Micro-Pattern Gaseous Detectors and their Applications, UNAM, Mexico.

Andiamonje, S. et al, Development and performance of Microbulk Micromegas detectors, 1st International Conference on Micro Pattern Gaseous Detectors, 2009, pp. 1-11.

Dolney, Derek, Novel Approaches to Address the Proton Beam Range Uncertainty, Penn Radiation Oncology, 2015.

Giomataris, I. et al, Micromegas in Bulk, CEA-DSM/Saclay-France, pp. 1-6.

Basile E. et al, An online proton beam monitor for cancer therapy based on ionization chambers with micro pattern readout, 2nd International Conference on Micro Pattern Gaseous Detectors, 2011, pp. 1-11.

Bihalowicz, Jan Stefan, 3D reconstruction of nuclear reactions using GEM TPC with planar readout, AIP Conference Proceedings 1645, 301-305 (2015); doi: 10.1063/1.4909590.

Alarcon, R. et al, Detectors for in vivo range and dose verification in proton therapy, International Journal of Modern Physics: Conference Series, vol. 44, 2016, 1660217 (9 pages).

Di Mauro, A. et al, Development of innovative micropattern gaseous detectors with resistive electrodes and first results of their applications, CERN, Geneva, Switzerland, pp. 1-13.

Bortfeldt, J., Development of Micro-Pattern Gaseous Detectors—Micromegas, Ludwig-Maximilians-Universitat Munchen, 2010 (117 pages).

Shepp, L. A. et al, The Fourier Reconstruction Op a Head Section, IEEE Transactions on Nuclear Science, vol. NS-21, Jun. 1974, pp. 21-43.

Fritsch, Adam Louis, The Search for Cluster Structure in 14C With the Prototype AT-TPC, Dissertation submitted to Michigan State University, Physics—Doctor of Philosophy, 2014 (182 pages).

Bachmann, S. et al, High rate X-ray imaging using multi-GEM detectors with a novel readout design, Nuclear Instruments and Methods in Physics Research A 478, 2002, pp. 104-108.

Titov, Maxim, Perspectives of Micro-Pattern Gaseous Detector Technologies for Future Physics Projects, Proceedings of the CMS Workshop "Perspectives on Physics and on CMS at Very High Luminosity, HL-LHC", Alushta, Ukraine, May 28-31, 2012.

Sauli, F. et al, Micropattern Gaseous Detectors, Annu. Rev. Nucl. Part. Sci. 1999. 49:341-88.

Ochi, A. et al, Development of imaging microstrip gas chambers and measurement of the polarization of X-rays, Nuclear Instruments and Methods in Physics Research A 391, 1997, pp. 124-126.

Alonso, J.R. et al, Computed Tomographic Reconstruction of Beam Profiles With a Multi-Wire Chamber, IEEE Transactions on Nuclear Science, vol. NS-26, No. 3, Jun. 1979.

Fraser, J.S., Beam Analysis Tomography, IEEE Transactions on Nuclear Science, vol. NS-26, No. 1, Feb. 1979.

Fessler, J., Analytical Tomographic Image Reconstruction Methods, Chapter 3, Nov. 19, 2009.

Alonso, J. et al, Complex Beam Profile Reconstruction, A Novel Rotating Array of Vibrating Wires, Proceedings of IPAC2014, Dresden, Germany, 2014.

Collins, P. R., Research and Development for Future Detectors, Nuclear Physics B (Proc. Suppl.) 117 (2003) 391-409.

Ropelewski, L., Gas Micropattern Detectors for Tracking, Cern, PH/DT2/ST.

* cited by examiner

IONIZING PARTICLE BEAM FLUENCE AND POSITION DETECTOR ARRAY USING MICROMEGAS TECHNOLOGY WITH MULTI-COORDINATE READOUT

RELATED APPLICATIONS

This application claims the benefit of U.S. provisional patent application 62/332,882, filed May 6, 2016 titled "Ionizing Particle Beam Fluence and Position Detector Array Using Micromegas Technology with Multi-Coordinate Readout" the entirety of the disclosure of which is incorporated by this reference.

TECHNICAL FIELD

This disclosure relates to an Ionizing Particle Beam Fluence and Position Detector Array Using Micromegas Technology with Multi-Coordinate Readout and a method of monitoring both the Fluence and Position of an Ionizing Particle Beam, such as with a Multi-Coordinate Readout.

BACKGROUND

Particle detectors include Micro-MEsh Gaseous or Micro-MeGas Structures (hereinafter "Micromegas"). A Micromegas detector is a gaseous detector, that like other gaseous detectors, detects particles by amplifying charges that have been created by ionization in a gas volume. An exemplary Micromegas detector 8 is shown in FIGS. 1A and 1B, in which FIG. 1A shows a schematic view of the Micromegas detector 8, and FIG. 1B shows a perspective view of the micromesh 12 supported over readout strips 14. In the Micromegas detector 8, a gas volume 16 can be divided in two by the metallic micro-mesh 12, which can be placed a distance d2 above a readout electrode, strip, or micropattern array of conductive readout pads, e.g., between 25 micrometers (μm) and 150 μm. The micro-mesh 12 can allow both a high gain, e.g., of $10^4$, and a fast signal, e.g., 100 ns, at a same time.

FIG. 1A, shows an ionizing particle or incident beam of particles 10. While passing through the detector 8, the particle(s) 10 will ionize gas atoms 20 by pulling up an electron 22 creating an electron 22/ion 20 pair. When no electric field is applied, the ion 20/electron 22 pair can recombine and nothing happens. However, when an electric field is present, such as in the order of 400 volts/centimeter (V/cm), the electron 22 can drift 24 toward the amplification electrode (micro-mesh 12) and the ion toward the cathode or cathode plane 26. When the electron 22 arrives close to the micro-mesh 12, the electron enters 22 an electric field (typically on the order of 4 kilovolts/cm (kV/cm) in the amplification gap d2). Accelerated by the electric field, the electron 22 reaches enough energy to produce ion/electron pairs that will also ionize the gas 16, creating pairs in what is known as the avalanche effect 28. Through the avalanche effect 28, several thousand ion/electron pairs are created from hundreds of primary charges, which originate from the interactions with the impinging particle, the primary charges being multiplied to create a significant signal. The electronic signal 30 is read at the readout electrode PCB anode plane 32 by a charge amplifier. The readout electrode 32 being conventionally segmented in strips and/or pixels 18 in order to obtain a position of the impinging particle in the detector 8. The amplitude and the shape of the signal 30, read via an electronic on the readout electrode or data acquisition electronics 34, can give information on the time and energy of the measured particle 10.

Thus, the incident beam of particles 10 ionizes gas 16 within detector chamber 8 drift volume d1 between the cathode plane 26 gas chamber volume cover with applied high-voltage bias HV1, producing primary ionization electrons 24. Free electrons 22 produced by ionizing particle beam 10, drift towards the biased (HV2<HV1) micromesh 12 that is located parallel to the micropattern array of conductive readout pads 18 on the surface of the array PCB anode plane 32. Once the drift electrons 22 reach the mesh 12, the greater potential difference between HV2 and the grounded array pads 18 accelerates them towards the readout array pads 18 through a narrow distance d2 while producing electron gas avalanches 28 with a high multiplication factor that is determined by the gap distance d2, a type of gas 16 used in the chamber 8, and the potential difference HV2 between the mesh 12 and array collector pads 18. The multiplied negative signal 30 can then being collected by the pads 18, and these amplified signals 30 can then be read out by the data acquisition electronics 34.

FIG. 1B shows a perspective view of the detector 8, which is a typical arrangement overview of the one-dimensional Micromegas array assembly, shown in FIG. 1A. FIG. 1B shows the planar PCB array board 32 with surface-routed readout strips 18 residing on thin regular pattern with pitch 6 of pillars 36 at a distance d2 under the parallel planar micromesh 12.

SUMMARY

A need exists for an improved particle beam detector system. Accordingly, in an aspect, a particle beam detector system can comprise a particle beam generator, a particle beam fluence and position detector array based on Micromegas technology, and data readout electronics coupled to the position detector array. The particle beam fluence and position detector array can comprise a sealed, gas-filled, ionizing radiation detector chamber. A printed circuit board (PCB) can be disposed within the ionizing radiation detector chamber, the PCB comprising a multi-layer array arrangement of interconnected conductive sensor pads comprising three planar coordinate grids, X, Y, and ST (stereo) situated on separate layers of the PCB. The multi-layer array arrangement of interconnected conductive sensor pads can comprise a first footprint. A dielectric lattice structure can be disposed over the PCB and the multi-layer array arrangement of sensors. A conductive mesh structure can comprise a second footprint disposed over the dielectric lattice structure and extending over an entire area of the first footprint.

The particle beam detector system can further comprise the multi-layer array arrangement of sensors comprising X, Y, and ST coordinates comprising a diamond shape such that a diamond shape X coordinate sensor, a diamond shape Y coordinate sensor, and a diamond shape ST coordinate sensor join to form a hexagonal shape. The dielectric lattice structure can comprise openings of any shape through which a particle beam may pass to the multi-layer array arrangement of sensors. The particle beam detector system can comprise a first number of electronic signal acquisition channels for resolving incoming flux intensity variations that is lower than a second number of electronic signal acquisition channels using individual independent collector pads for which the second number of independent collector channels increases by a power law. The detector array can comprise a curved surface to produce a cylindrical detector.

The dielectric lattice structure can comprise a wall thickness in a range of 0.003-0.5 millimeters (mm) and a height in a range of 50-300 micrometers (µm). The particle beam generator can be adapted to send an ionizing particle beam to the detector array, and the position detector array can be oriented substantially perpendicular to a direction of a beam produced by the particle beam generator.

In another aspect, a particle beam detector array can comprise a sealed, gas-filled, ionizing radiation detector chamber, and a substrate disposed within the ionizing radiation detector chamber. The substrate can comprise a multi-layer array arrangement of sensors comprising three planar coordinates X, Y, and ST situated on three layers of the substrate. A dielectric lattice structure can be disposed over the substrate and the multi-layer array arrangement of sensors. A conductive mesh structure can be disposed over the dielectric lattice structure.

The particle beam detector array can further comprise the multi-layer array arrangement of sensors comprises a first footprint, and the conductive mesh structure can comprise a second footprint disposed over the dielectric lattice structure that extends over an entire area of the first footprint. The multi-layer array arrangement of sensors comprising X, Y, and ST coordinates can comprise a diamond shape such that a diamond shape X coordinate sensor, a diamond shape Y coordinate sensor, and a diamond shape ST coordinate sensor join to form a hexagonal shape. The dielectric lattice structure can comprise openings of any shape through which a particle beam may pass to the multi-layer array arrangement of sensors. The particle beam detector system can comprise a first number of electronic signal acquisition channels for resolving incoming flux intensity variations that is lower than a second number of electronic signal acquisition channels using individual independent collector pads for which the second number of independent collector channels increases by a power law. The multi-layer array arrangement of sensors can comprise a curved surface to produce a cylindrical detector. The dielectric lattice structure can comprise a wall thickness in a range of 0.003-0.5 mm and a height in a range of 50-300 µm.

In another aspect, a method of using an ionizing particle beam detector system can comprising directing an ionizing particle beam from a particle beam generator to a particle beam fluence and position detector array. The ionizing beam can be directed in a direction substantially perpendicular to the position detector array. The ionizing particle beam fluence and position can be measured with a particle beam fluence and position detector array. The particle beam generator can be calibrated by adjusting particle beam generator to generate an ionizing particle beam comprising a fluence and position within one percent of a desired fluence and position.

The method of using an ionizing particle beam detector system can further comprise directing an ionizing particle beam from the particle beam generator to a patient after uniquely calibrating the particle beam generator to radiate a tumor in the patient. A first ionizing particle beam can be directed from the particle beam generator to a first position on the particle beam fluence and position detector array. A first amount of radiation delivered can be measured by the first ionizing particle beam. The particle beam generator can be moved and a second ionizing particle beam can be directed from the particle beam generator to a second position on the particle beam fluence and position detector array. A second amount of radiation delivered by the second ionizing particle beam can be measured. A planar map of fluence for the radiation delivered by the first ionizing particle beam and the second ionizing particle beam can be generated. The ionizing particle beam can be generated with a fluence on the order of $10^5$-$10^{14}$ ionizing particles per second. A beam position and spot size can be resolved to 0.8-1.2 mm, and measure of delivered dose radiation with an accuracy of less than or equal to 2% of a desired dose for beam monitoring of proton therapy. A particle beam fluence and position detector array can comprise an active area greater than 10 centimeters squared ($cm^2$), a coordinate resolution (X, Y) less than 200 µm (Isotropic in X-Y), a beam flux dynamic range $10^6$-$10^{13}$ particles/$cm^2$/s±1%, a lifetime accumulated dose exposure greater than 50 kGy, a charge sensitivity less than 100 fC, and a response time less than 1 ms.

DETAILED DESCRIPTION

Figure 1A:
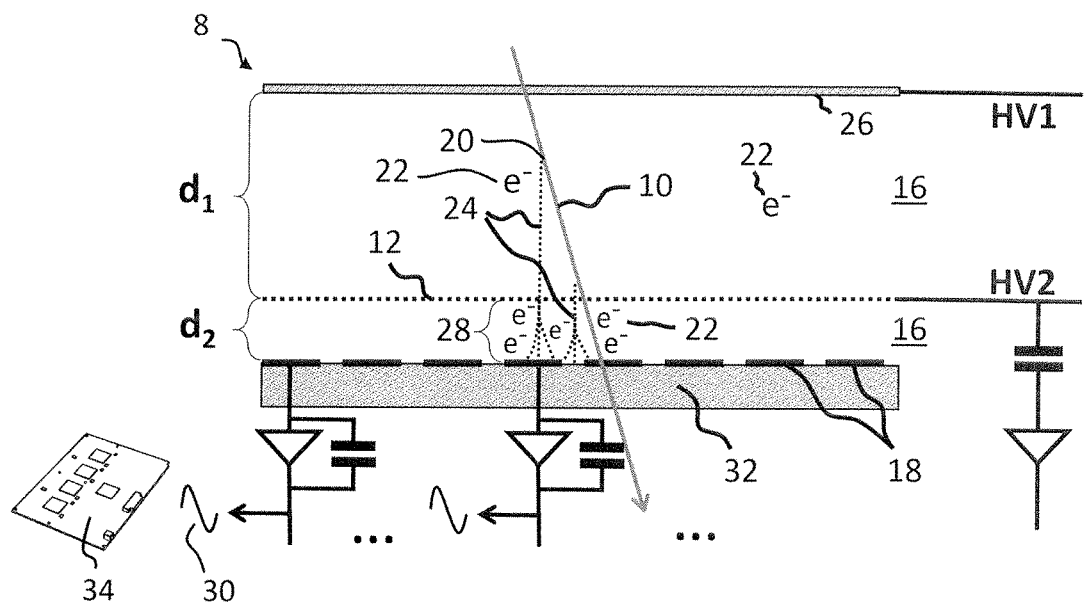
FIGS. 1A and 1B show operation of a Micromegas detector as known in the prior art.

This disclosure relates to a particle detector and a system and method of using the same. Particle detectors can be used to detect a passing particle and to obtain information about the particle, such as its position, arrival time, and momentum. The particle can come from a particle accelerator, from space (such as a cosmic ray), from a nuclear reactor, or from any other suitable source. Particle detectors include Micromegas and Segmented Wire Ion Chambers (SWICs). More specifically, this disclosure relates to ionizing particle beam fluence and position detector array using the Micromegas technology with multi-coordinate readout. It is intended that the concepts and principles further explained in this disclosure will be applied to the disclosures of the above referenced application by those of ordinary skill in the art.

This disclosure, its aspects and implementations, are not limited to the specific package types, material types, or other system component examples, or methods disclosed herein. Many additional components, manufacturing procedures, and assembly procedures known in the art consistent with semiconductor manufacture and packaging are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation. For example, while the discussion makes emphasis on proton therapy in particular, the proposed design could be adapted for other particle types, and used in a wide variety of applications in both science and industry.

The word "exemplary," "example" or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented, but have been omitted for purposes of brevity.

Applicant has understood that the instrumental problem of measuring both precise transverse position of a particle beam and its fluence (intensity) has been a long-standing experimental challenge. While hardly any instrument is truly universal with respect to varying dynamic range requirements and resolution, a versatile, mechanically robust device that is radiation-resistant and relatively inexpensive, can find a wide array of applications in both scientific and academic experiments as well as in commercial applications.

A gas-filled ionizing radiation detector, based on the Micromegas technology can provide the required or desired resolution in both two-dimensional transverse plane (extendable to three dimensions) and radiation fluence measurement domains, ensure low transparency to minimize the perturbation on the impinging particle beam and radiation resistance, withstanding exposure to radiation doses of over 50 kGy (equivalent to ~5 yrs. of clinical use) with minimized deterioration of performance over time. A proposed multi-layer array arrangement is designed to provide high coordinate position resolution with fewer electronic readout channels, resulting in a cost-efficient instrument that will possess significant advantages over existing commercial solutions, most of which use solid-state detector technologies.

Since radiation flux stops in the body of a patient, the particle beam profile, depth, and intensity, are difficult quantities to measure. This contrasts with photon therapy where the exiting radiation can be easily measured. This measurement limitation for hadron therapy forces treatment planning to be overly cautious, thereby limiting the overall effectiveness of hadron therapy. Currently, oncologists and medical physicists mostly depend on calculation and internal beam measurements (measurements made by the delivery system) to assure the quality of care. Moreover, patient treatment planning will typically occur only once over the entire course of treatment due to time and cost. Applicant's insights and improvements provide for precise external measurement which will inform oncologists and medical physicists of treatment delivery, and fulfill a long felt need.

Direct detection and measurement of high beam currents used for hadron treatment can be supplied by a new generation of detector devices capable of high spatial and time resolution accompanied by good linearity and very wide dynamic range in the Bragg peak position measurement. A first measurement provided by Applicant's system can establish (a) conformity of transverse beam position (in X-Y) and fluence (intensity) profile, and (b) precision of energy modulation of proton beam. Furthermore, use of the proposed fluence detector followed with a multi-plate ionization chamber will allow the capabilities of Applicant's system be a universal 3-D dose and fluence instrument for quality assurance (QA) of therapeutic heavy ionizing particle beams as well as photon beams.

Gaseous detectors can be advantageously used when particle detection devices are desired because gaseous detectors can provide large area coverage, high counting rates, linearity, and low material budget. Applicant's system provides high radiation damage resistance, and excellent spatial and time resolution making gaseous detectors a valuable tool to meet the growing technical demands at the frontiers of research. Designs of new micro-pattern devices can also be well-suited for bulk industrial production processes, which can allow for applications in a wide array of industrial and general radiation detection tasks as well as commercialization.

Micromegas chambers have a number of advantages when compared to multi-wire proportional chambers (MWPC), the first MWPC design invented in 1968 by G. Charpak (with the Nobel Prize awarded in 1992). For instance, the amplification gain of the Micromegas shows low sensitivity to geometrical parameters, such as the gap size, which reduces the influence of fluctuations or uncertainties of the parameters on the gain, giving a higher stability over time and better spatial uniformity. Another advantage is Micromegas' capability for high particle flux rate applications. For example, Micromegas reduce an ion backflow fraction and slow ion signals because positive ions created in the avalanche are collected by the cathode mesh in a short time, typically around 100 nano-seconds (ns).

Measuring both a precise transverse position of a particle beam and its fluence (intensity) is an experimental challenge faced by measurement instrumentation. Measurement instrumentation can often be limited with respect to varying dynamic range requirements and desired resolution. As such, the system, method, and device described herein can be a versatile mechanically robust device that is radiation-resistant and relatively inexpensive, which can be applicable in a wide array of applications including scientific or academic experiments, as well as in commercial applications.

Applicant's system, method, and device, which comprises an Ionizing Particle Beam Fluence and Position Detector Array using the Micromegas Technology with Multi-Coordinate Readout, and for convenience can also be referred to hereinafter as a particle beam detector system, Applicant Array, or Array, relates to a practical problem of quality assurance in cancer treatment with proton beams in clinical proton accelerators. Applicant's Array can comprise a gas-filled ionizing radiation detector, similar in some respects to the Micromegas technology, and can provide desirable resolution in both 2D spatial (3D spatial) and fluence domains. Applicant's array can ensure low transparency to minimize perturbation on an impinging particle beam and radiation resistance. Applicant's array can withstand exposure to radiation doses of over 50 kGy (equivalent to ~5 yrs. of clinical use) with limited or minimal deterioration of performance over time. A proposed multi-layer array arrangement, discussed in greater detail below, is designed to provide high coordinate position resolution with fewer electronic readout channels, which results in the Array being a cost-efficient instrument that possess significant advantages over existing commercial solutions, including solid-state detector technologies.

In some instances, the Array comprises millimeter and millisecond resolution and high dynamic range. When used as a beam monitoring device for proton therapy, beams can comprise a transverse beam position and spot size be resolved to a size of about 1 mm, such as 0.8-1.2 mm, and deliver doses measured with an accuracy of 2% or more. In some embodiments, the Array can comprise an active area greater than 10 cm$^2$, a coordinate resolution (X, Y) less than 200 μm (Isotropic in X-Y), a beam flux dynamic range $10^6$-$10^{13}$ particles/cm$^2$/s±1%, a lifetime accumulated dose exposure greater than 50 kGy, a charge sensitivity less than 100 fC, and a response time less than 1 millisecond (ms).

Figure 2A:
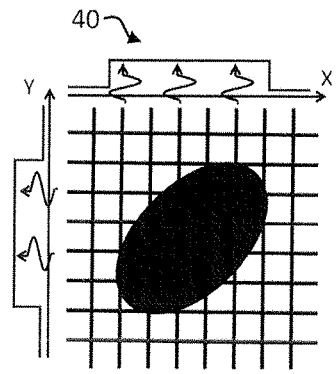
FIGS. 2A-2C show various sensor arrangements in which a number of readout channels vary.
Figure 2B:
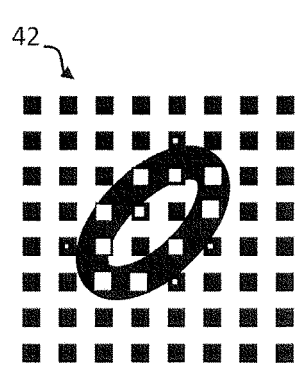
Figure 2C:
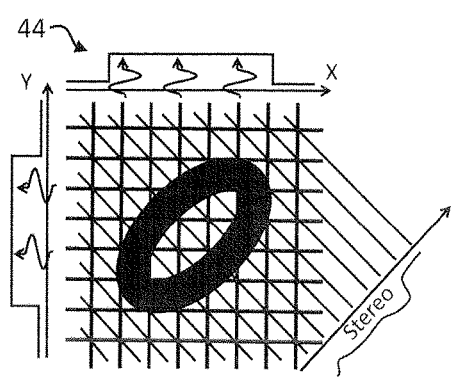

Applicant's particle beam fluence and position detector array based on Micromegas technology, particle beam fluence and position detector array, detector array, or device ("Detector," "Device," or "Array") can resolve complex cross sectional ionizing particle fluence variations by having sensitivity in three planar coordinates via three groups of sub-pads 56, situated on or over a surface of a PCB or substrate 58 with the three coordinate grids instrumented each on a separate layer (such as on one of three inner layers) of the PCB or substrate 58. For convenience, and not by way of limitation, the three planar coordinates as X, Y, and ST (stereo) are used and shown. FIGS. 2A-2C show generally, schematic differences between (i) a two-coordinate readout via strip-shaped charge collector pads 40 shown in FIG. 2A, (ii) individual independent collector pads 42 shown in FIG. 2B, and (iii) three-coordinate readout or array 44, or an embodiment of Applicant's Array configuration shown in FIG. 2C. More specifically, FIG. 2A shows the 2-coordinate x-y readout 40 with only 16 readout strips connected to separate electronic data acquisition channels each, in which few channels are used and the creation of a possible complex fluence map structure is not available. FIG. 2B shows the readout of individual pixels 42, such as a diode array, in which there are 64 ($8^2$) readout channels, good resolution, but uses a large number of channels, the number of channels increasing by the power law as the array size increases, making the number of channels cumbersome, impractical, or unusable for desired applications. FIG. 3C shows the 3-coordinate X-Y Stereo Readout 44 in which there are 31 (8×4-1) readout channels providing very good resolution using convolved information from each directional coordinate projection of the initial ionization signal from readout strips connected to separate electronic data acquisition channels. An advantage of having an ST layer as shown in FIG. 2C is that the arrangement allows for resolving possible complex incoming flux intensity variations while at the same time keeping the number of electronic signal acquisition channels low with comparison to arrays with individually connected collector pads.

Figure 3A:
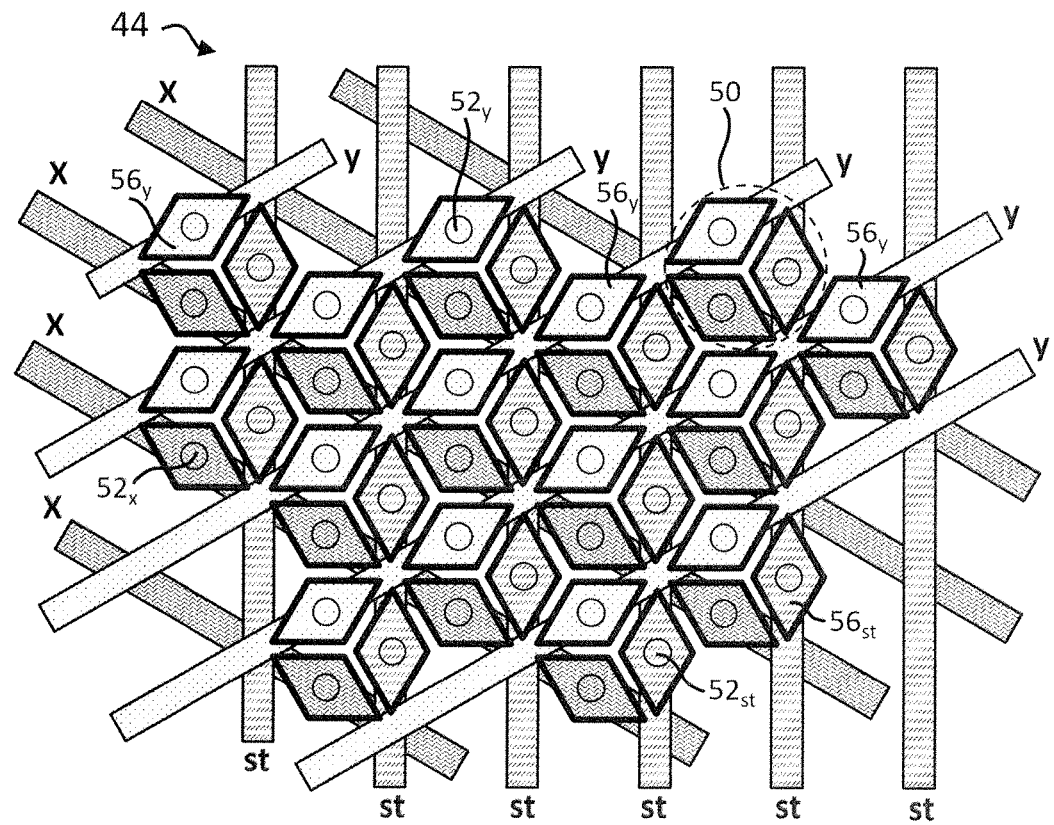
FIGS. 3A-3F show various views of an embodiment of a three-coordinate readout array.

An example of Applicant's three-coordinate array of collector pads, pad clusters, or super-cluster pads 50 is shown in FIG. 3A. The vias, or vertical conductive connectors 52 (such as vias or connectors 52x, 52y, and 52st) are shown as circular columns, posts, or cylinders, that lead pad connections to their respective strips 54 (such as strips 54x, 54y, and 54st). While the vias 52 are shown being circular or cylindrical in shape, any suitable shape can be used.

FIG. 3A shows, the three-coordinate array, particle beam fluence and position detector array based on Micromegas technology, a particle beam fluence and position detector array, a detector array, or device 44 comprising geometrically interlocking conductive pad clusters 50 consisting of three small sub-pads 56 (such as sub-pads 56x, 56y, and 56st), with series of the corresponding sub-pads 56 being interconnected amongst all clusters 50 along the three distinct directions (X, Y, and ST) in their separate layer of circuit board by the individual vias 52. The use of an interlocking arrangement or pattern of conductive pad clusters 50 differs from the conventional approach of relying solely on cross-locking patterns of (resistive) strips 14 separated by insulating layers as shown in the arrangements of FIGS. 2A and 2B. The interlocking pattern of array 44 can form hexagonal clusters 50, with each of hexagon being divided in three parallelogram-shaped or diamond shaped collectors 56 that allow for maintaining good coordinate resolution, as shown in FIG. 3A. While the array 44 and super-clusters 50 can be arranged in hexagonal configurations as shown, any other suitable arrangement can also be used including square, triangular, diamond, rectangle, rhombus, trapezoid, circle, oval, or any other suitable geometric or organic shape. Whatever the shape and arrangement of clusters 50, such as hexagons, attention can be given to improve charge sharing amongst the neighboring clusters 50 or pads 56, while being able to resolve the ambiguities in signal amplitude along each of three coordinate strips 54 or vias 56 factoring in additional information from the other two (or more) neighboring crossings, depending on the complexity of the fluence profile and cross section that is being evaluated. With the size of the sub-pads 56 sufficiently small (on the order of several $mm^2$, such as 1-7 $mm^2$, 2-6 $mm^2$, or 3-5 $mm^2$) linear resolution across the array could be on the order of few hundred microns, such as 100-1000 μm, 150-80 μm, or 200-600 μm. With each of the readout strips in each coordinate grid being connected to a respective known electronic data acquisition registration channel, charge collection by way of a crossing series of conductors can operate in a way similar to a segmented wire ion chambers (SWICs) with segmentation being implemented across the array plane 44 rather than a counting gas volume that ionizing particle beam traverses.

When arranging the Arrays with geometrically interlocking conductive pad clusters 50 as shown and described, design of the Micromegas array 44 can operate with several distinct biasing schemes, with a possibility of biasing collector pads or having them at ground potential, as well as operating in reverse bias, depending on particular experimental demand, beam conditions, and application. These possibilities are targeted to make Applicant's device and arrays more versatile, and operate as a more universal experimental tool.

The array 44 of FIG. 3A has series of diamond-shaped pads or sub-pads 56 with rows of the pads 56 that correspond to each of the three planar coordinates x (56x), y (56y), and ST (56st) in three different directions in the array plane 44, and are being interconnected by means of conductive traces or strips 54. In this arrangement, each set of the diamond-shaped pads 56 in x, y, and st, form hexagon-shaped detection clusters 50.

Figure 3B:
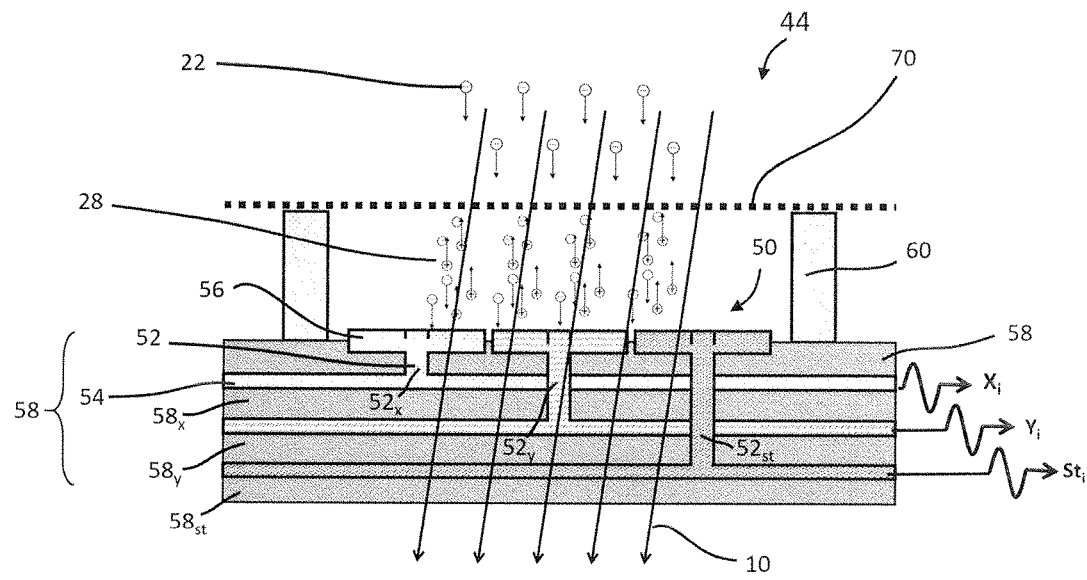
Figure 3C:
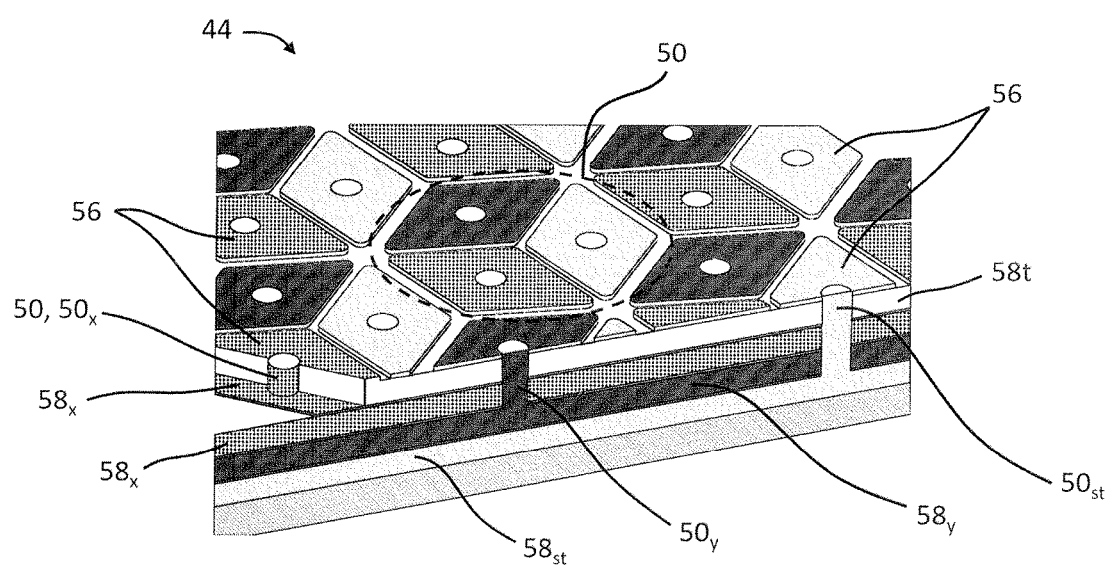

FIG. 3B shows a cross-sectional profile view of the array 44 from FIG. 3A in which each of the interconnecting series of traces 54 may be disposed in a separate layer of a multi-layer printed circuit board, array PCB, substrate, carrier, or interconnect structure 58, which for convenience and not by way of limitation may be referred to hereinafter as a PCB 58. Pads 56 in each of the corresponding coordinates, x, y, and st, make connections to the conductive traces 54 for each of the coordinate positions, by means of the interconnecting vias 52. Additional PCB layers may contain grounds and shielding. The mutual superposition and angle of the interconnecting coordinate directions, x, y, and st, may not necessarily have any particular value for the angle(s) and shall be adapted to a particularly desired device performance.

Stated another way, FIG. 3B shows a drifting ionization signal approaches the positively biased micromesh 70 and passing though the gain region with the distance d2 defined by a thickness of a dielectric lattice, separator, mesh, layer, film, pad, mat, framework, stencil, or structure 60 or distance d2, is being collected by the pads 56 within the three-coordinate hexagon-shaped detection clusters 50. The micromesh 70 can be formed of a conductive material, such as metal like aluminum (Al), copper (Cu), tin (Sn), nickel (Ni), gold (Au), silver (Ag), iron (Fe) or other suitable material. The micromesh 70 can be a fine conductive bias mesh structure, included within the perimeter frame 136 or not, disposed over the dielectric lattice 60, and extending over an entire area of the multi-layer array arrangement 44. The conductive mesh or micromesh 70 can comprise a footprint disposed over the dielectric lattice structure 60 and extending over an entire area of a footprint of the array 44.

FIG. 3C, shows a partial cross section of the array PCB 58, layers 58t, 58x, 58y, and 58st, showing the interconnecting vias 52 from the pads 56 to the conductive traces 54 for each of the separate coordinate planes (layers) x, y, and st.

Figure 3D:
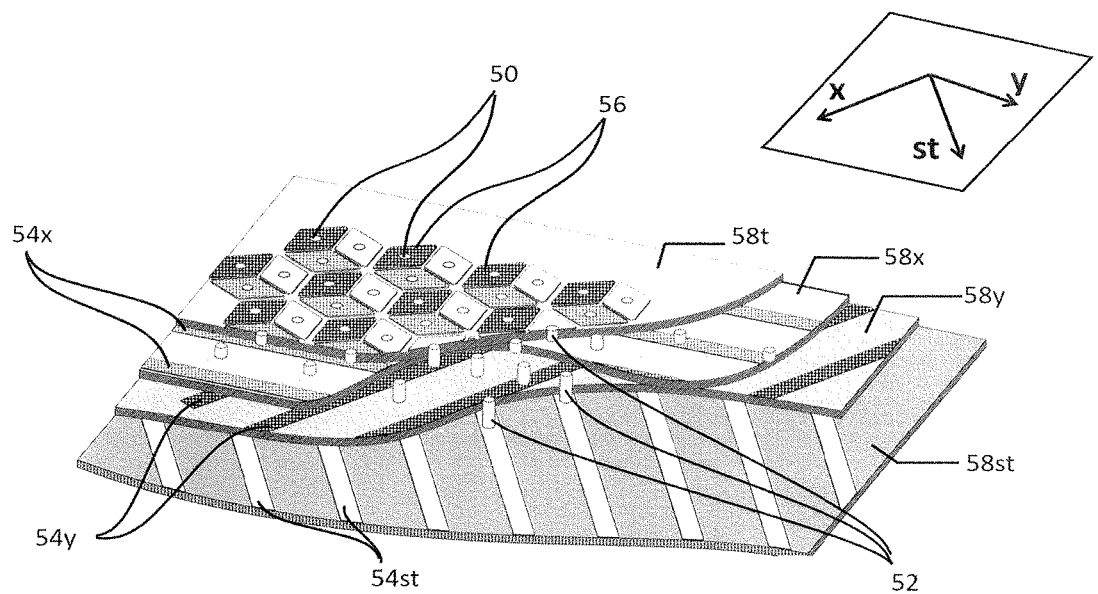

FIG. 3D shows array pads 56 forming detection clusters 50, with a cut away view of the clusters 50 being coupled to series of coordinate conductive traces 54 on various layers of the PCB 58, being interconnected by various layers of conductive vias 52.

Figure 3E:
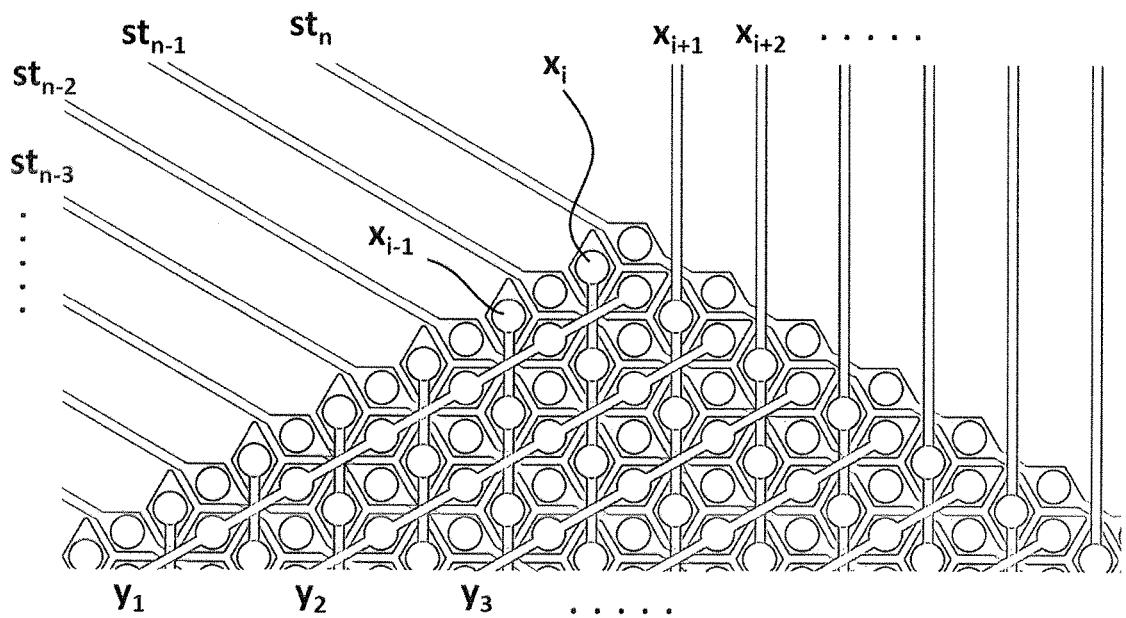

FIG. 3E shows a particular implementation detail of the array 44 on the layout of the PCB 58, in which the array outline of clusters 50 is defined as a hexagonal shape, from portions of the sub-pads 56, in order to keep most of the interconnecting traces 54 to the same or similar length in order to avoid large variation in capacitance and signal path for different channels x, y, and st.

Figure 3F:
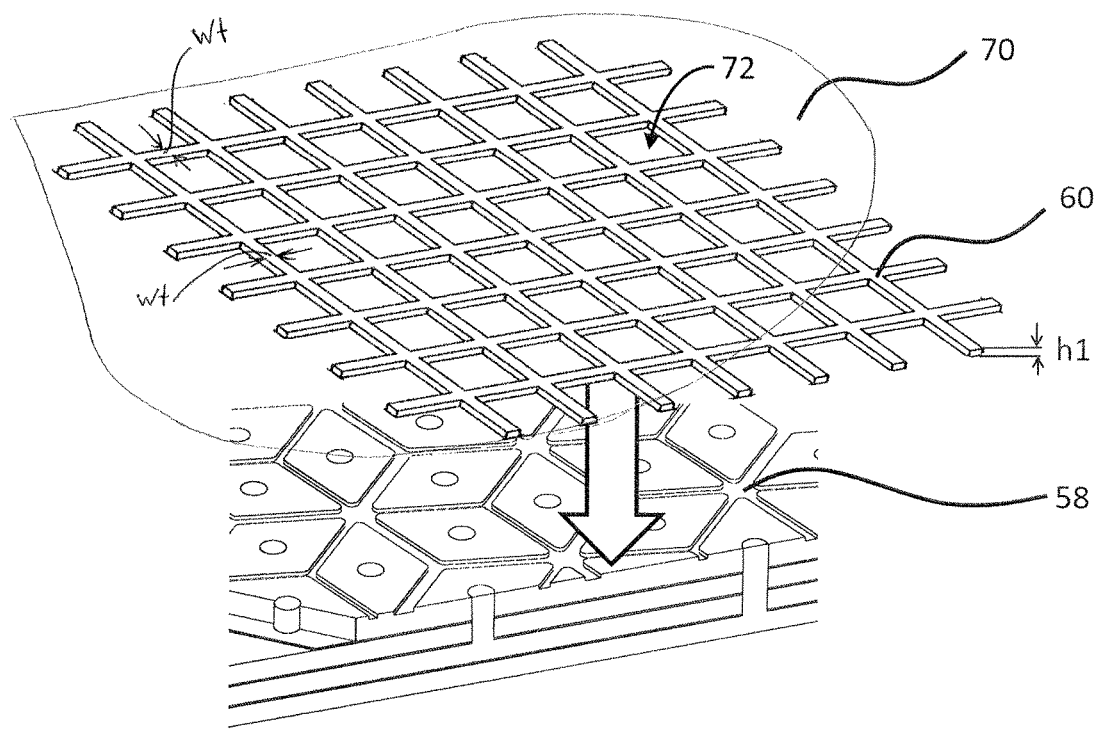

FIG. 3F shows the lattice 60 may be used to define the stand-off distance d2 between the PCB array board 58 and the bias micromesh 70 so that micromesh 70 rests parallel to the PCB array board 58 in a highly stable and regular manner. The height h1 of lattice 60 can be equal to d2, or the height of pillars 36. The height h1 can be constant, fixed, uniform, or substantially so, varying less than 10%, 5%, 2%, 1%, or 0.5% of the height h1 of the lattice 60 while a length and width of the lattice 60 can be of any desirable distance to extends in directions perpendicular, orthogonal, or transvers to the height h1 and across the array PCB 58. The lattice 60 can also comprise mesh elements 64 comprising comprises a wall thickness wt in a range of 0.003-0.5 mm.

While the dielectric lattice 60 is shown with square openings 62 in the lattice 60, the lattice 60 can be arranged with any shape and with any size openings 62, including rectangular, triangular, diamond, rectangle, rhombus, trapezoid, circle, oval, or any other suitable geometric or organic shape. Similarly, the dielectric lattice 60 can be made of, and the openings 62 defined by mesh elements 64 that can comprise any suitable cross-sectional area and shape, including square, rectangular, triangular, diamond, rectangle, rhombus, trapezoid, circle, oval, or any other suitable geometric or organic shape. A size or area of the sub-pads 56 may be on the order of several $mm^2$, such as 1-7 $mm^2$, 2-6 $mm^2$, or 3-5 $mm^2$. A fine dielectric lattice structure 60 can be formed fine enough, with large enough openings 62 and small enough mesh elements 64, that the lattice 60 can overlap or cover portions of sub-pads 56 while still allowing the sub-pads 56 and the pad clusters 50 to receive adequate signal, or radiation from beam 10.

Figure 1B:
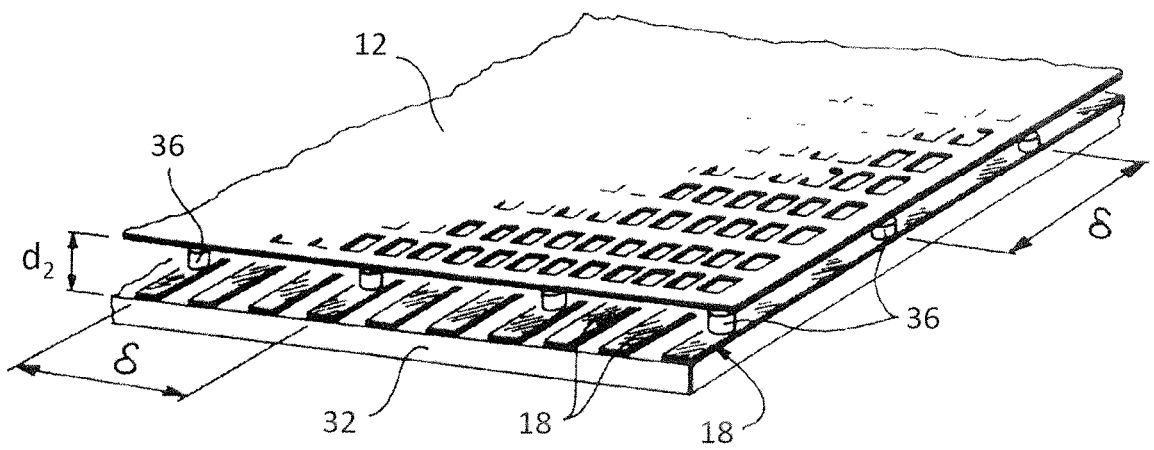

The dielectric lattice can be made of a layer, film, sheet, or other form of one or more layers of silicon dioxide ($SiO_2$), silicon nitride ($Si_3N_4$), silicon oxynitride (SiON), tantalum pentoxide ($Ta_2O_5$), aluminum oxide ($Al_2O_3$), hafnium oxide ($HfO_2$), polyimide, Kapton®, benzocyclobutene (BCB), polybenzoxazoles (PBO), dielectric film material, or other material having similar insulating and structural properties, including a photosensitive dielectric polymer. The lattice can be made or formed with the positive and negative spaces being arranged at a same time through an additive, growth, or build-up process such as such as 3D printing, or other suitable process where successive layers or materials can be added to form the lattice 60. In other instances, the openings 62 can be formed, such as by removing material from a base material such as a film, sheet, or in another form, so as to form the lattice 60. Removal of material to form the openings 62 can be done chemically, mechanically, or both. For example, a layer of material can be laser cut, so as to form, e.g., a Kapton laser-cut stencil. Thus, the lattice 60 can in some instances can also be referred to as a flat or planar periodic lattice structure 60. The lattice 60 can also be more robust, durable, or both, than using discrete pillars 36 as shown in FIG. 1B.

Figure 4A:
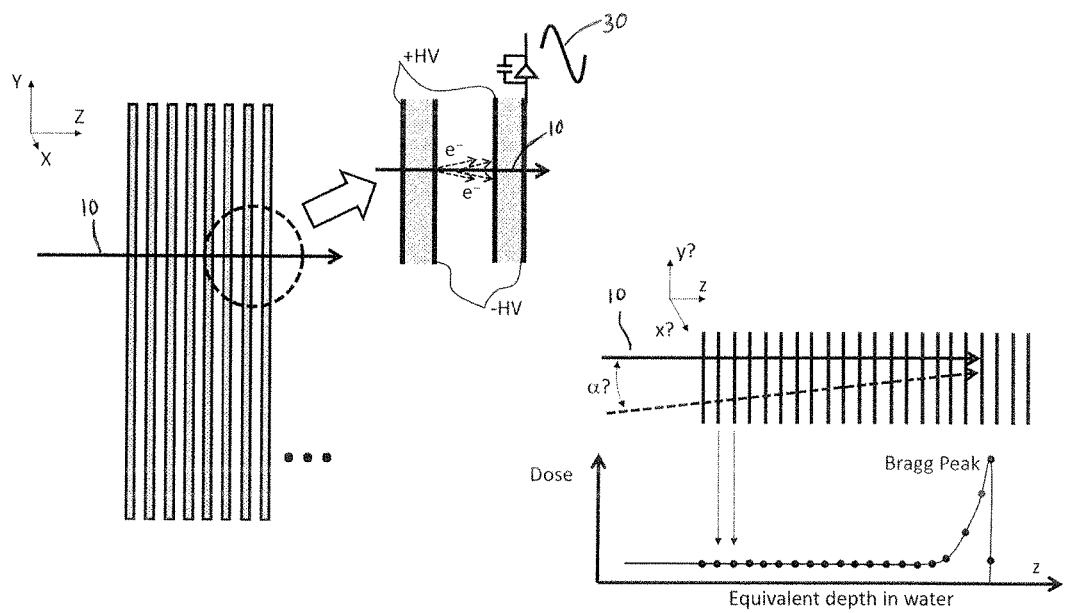
FIGS. 4A-4C show an embodiment of a multi-layer ionization chamber.

FIG. 4A, shows a multi-layer ionization chamber with depth measurements for depth dose, range measurements of protons and heavy ions, in which the final dose volume position may be unknown and are not being measured. The multi-layer ionization chamber can comprise alternately biased planes than form layered ionization chambers. More specifically, FIG. 4A shows that beam 10 can produce an ionization signal 30 that is collected such as with data acquisition electronics 34, the ionization signal or hadron beam 10 being proportional to the deposited dose of the beam 10, that is the energy loss in the matter through which the beam 10 passes. FIG. 4A also shows a beam transverse profile and X-Y position, and the angle of incidence (and hence the final dose volume position) in a body are unknown in this case, and the angle of incidence (alpha) cannot be determined as to whether the angle of incidence was normal to the detector z-axis.

Figure 4B:
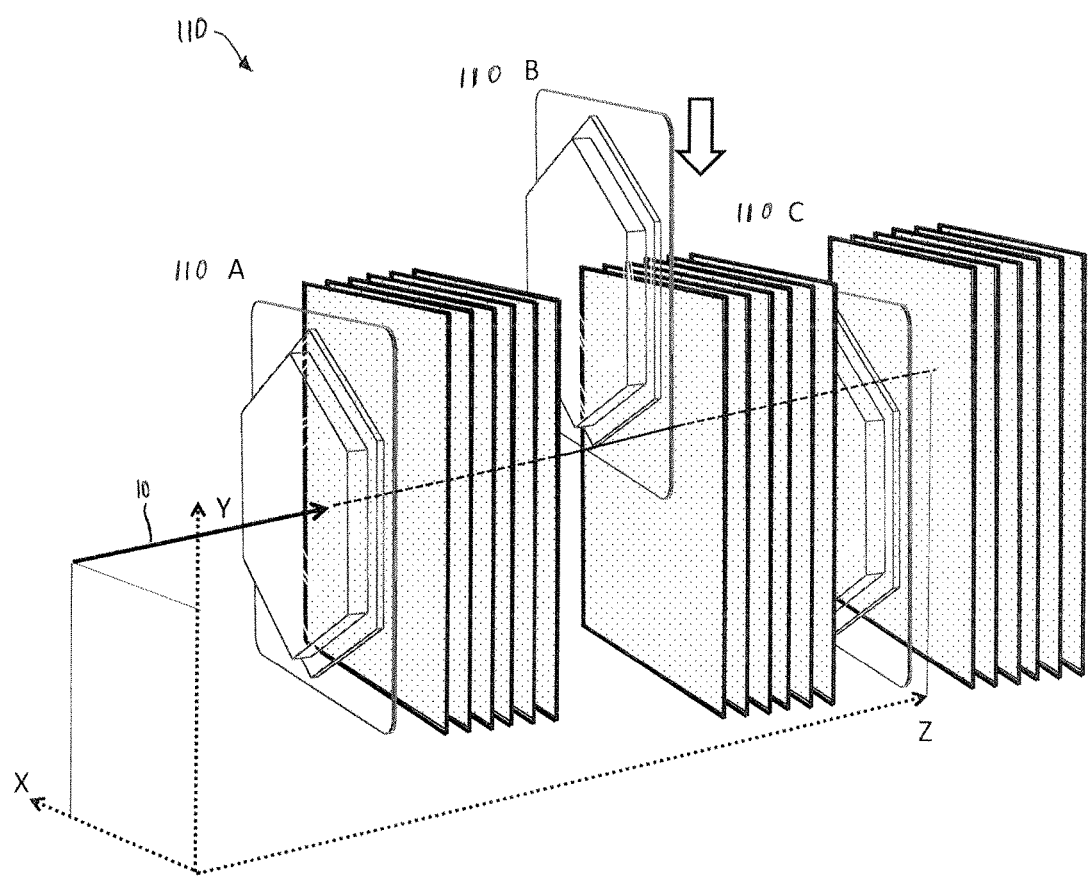

FIG. 4B, shows an embodiment of Applicant's Array or Device 110 as an improvement to a conventional multi-layer ionization chamber. In Applicant's Array depth dose measurements, and position, beam profile, and angle of incidence information is available. In Applicant's Device, a plurality of arrays, such as three arrays, 110 A, 110 B, and 110 C, are arranged with a hexagonal shape as a complete array or pattern of the super-cluster pads shown in FIGS. 3A and 3C. The super-cluster pads 50 comprise a cluster or grouping of a plurality of pads, such as three pads, each pad associated with, or for, measuring a different direction, such as an x-direction, a y-direction, and an st-direction. Arrays, 110 A, 110 B, and 110 C, which include the aforementioned three-coordinate readout planar Micromegas arrays of segmented 'super-cluster' pads 50, are arranged in a multi-layer ionization chamber 170, which can include a conventional multi-layer ionization chamber. With the plurality of multi-layer ionization detectors, transverse beam profile, beam direction of incidence (reconstructed by positions beam crossed arrays 110 A, 110 B, and 110 C), and X-Y position, as well as the energy loss (i.e. equivalent depth dose distribution) additional measurements are available, including measurements needed in most clinically significant use cases of proton radiation therapy.

Figure 4C:
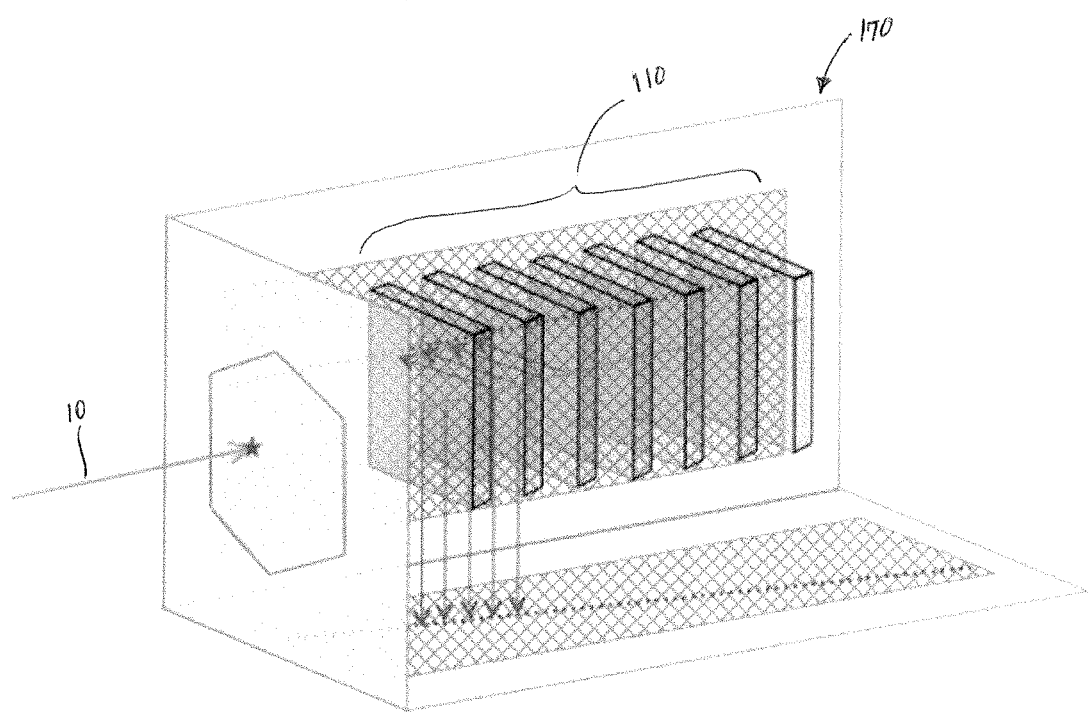

FIG. 4C, shows another arrangement of Applicant's Device or Array similar to the view shown above in FIG. 4B, including improvement to extend the three-coordinate segmented readout Micromegas array detector to 3D by arranging 3 planar arrays in orthogonal arrangement inside a single gas volume. FIG. 4C additionally shows alternating energy absorber blocks (water-equivalent plastic as an example material) that can be used to decelerate beam particles 10, and two planes XZ and YZ (each shown with cross-hatched pattern) than can be used as time projection chambers, when bias is applied alternatively to either one of those arrays of pads to produce separate projections.

Figure 5A:
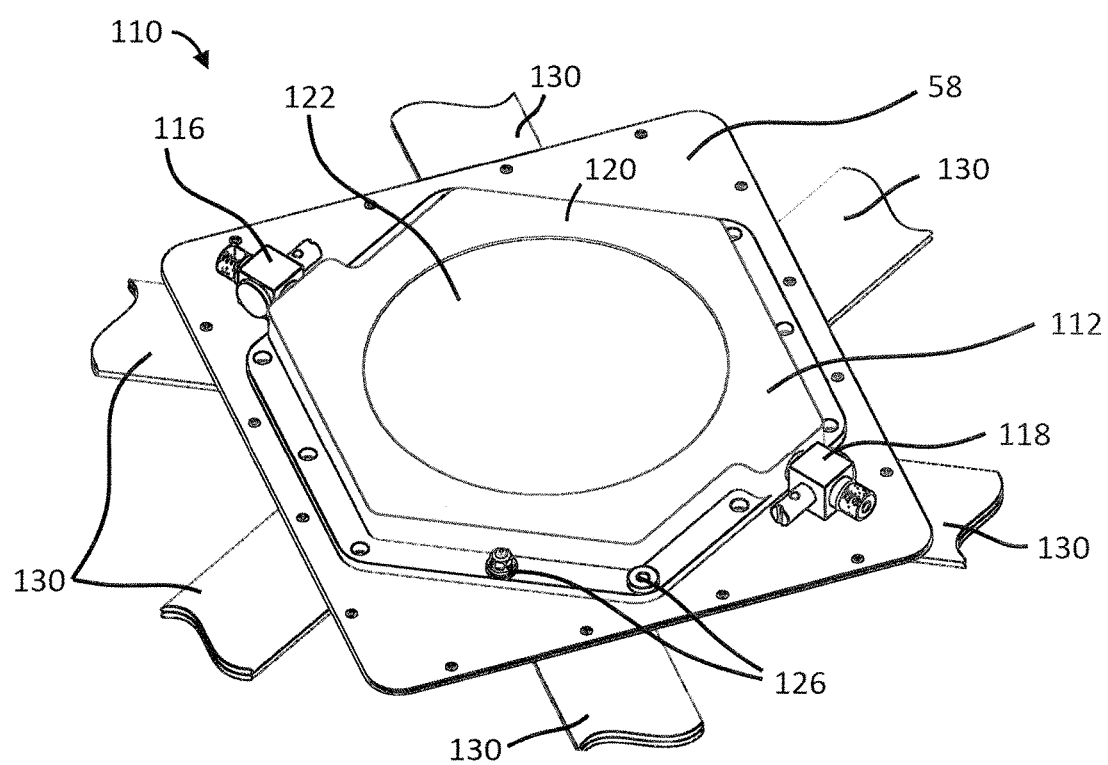
FIGS. 5A-5D show various views of an embodiment of a detector array or device.

FIGS. 5A-5D show an embodiment of the mechanical design of Applicant's particle beam fluence and position detector array based on Micromegas technology, a particle beam fluence and position detector array, a detector array, or device 110, although certain technical elements and features may not be displayed in full detail. FIG. 5A shows a non-limiting example of a top perspective view of a detector device 110. The detector device 110 comprises the detector array PCB 58, a detector gas volume 112, which can be similar to gas volume 16 described herein, the gas volume 112 further comprising inlet gas valve 116 and an outlet gas valve 118. The detector device can further comprise a recessed thin beam window 122 which may be integrally formed of a single unitary piece, such as being molded or machined in the same piece of material as the gas cover 120. The gas cover 120 can be coupled to the PCB 50, or held in place by mechanical or chemical attachment devices, adhesives, or fasteners, including a set of electrically-insulating hardware or fasteners 126. Signal readout and bias/ground connection can be made by or through custom-built cables 130 that can be coupled or directly attached or directly contacting a bottom of the array PCB 58 via through-hole mounted high-density data connectors 132. The coordinate readout strips 54, formed as layers over or within the PCB or substrate 58, each being routed to a dedicated pin contact within each of the data connectors 132.

At the center of FIG. 5A, and through window 122, is a position of the hexagonal array PCB 58, as shown in FIGS. 3A-3F and FIG. 6. As such, the array PCB 58, including hexagonal array structures shown within the device of FIGS. 5A-5D include the multi-layered or multi-tiered structure 44 with three layers or any other suitable number of vertically stacked or offset arrays. FIG. 5A also shows gas valves 116 and 118. Typical gases used within the device 110 can vary to include any suitable gas or gasses depending on the application, and will include gasses with desirable attributes, such as being non-toxic, low flow, easy to maintain, and providing good electron amplification gain. In some instances, a Methane-Argon mixture called P10 (10% Methane) can be used. P10 is non-toxic, low flow, easy to maintain, and provides good electron amplification gain.

Figure 5B:
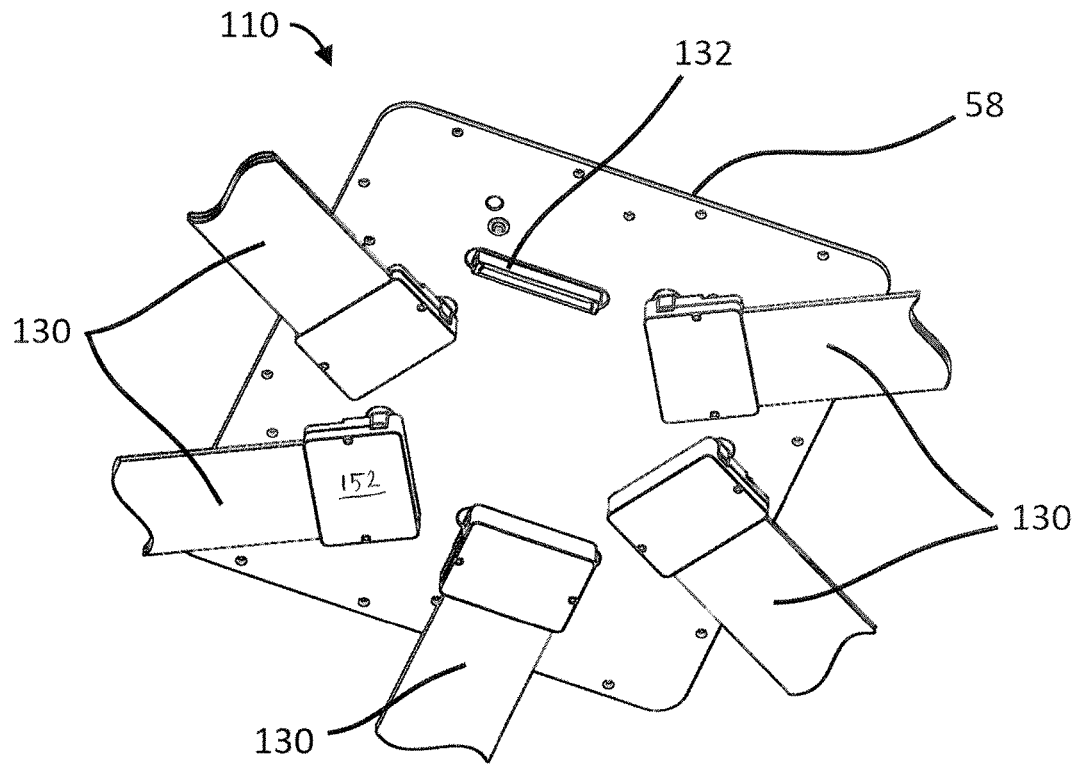

FIG. 5B shows a perspective view of the Device opposite the view shown in FIG. 5A, and includes the additional detail of ZAP connectors being coupled to the device. The ZAP connectors can be coupled to a ZAP board that provides spark protection for the data readout electronics and decouples low current signal readout and high-voltage bias.

FIG. 5B also shows a bottom perspective view the detector device 110 from below the detector array PCB 58 (which can comprise, without limitation, Kapton bonded to an aluminum substrate. Six custom-built signal-bias-ground cables connecting to the ZAP (signal, bias, ground distribution, and spark protection) board via high-density, through-hole, hermetically sealed connectors 132 that feed the signals and bias through the PCB board 58 in and out of the sealed gas volume 112 of the sealed detector 110.

Figure 5C:
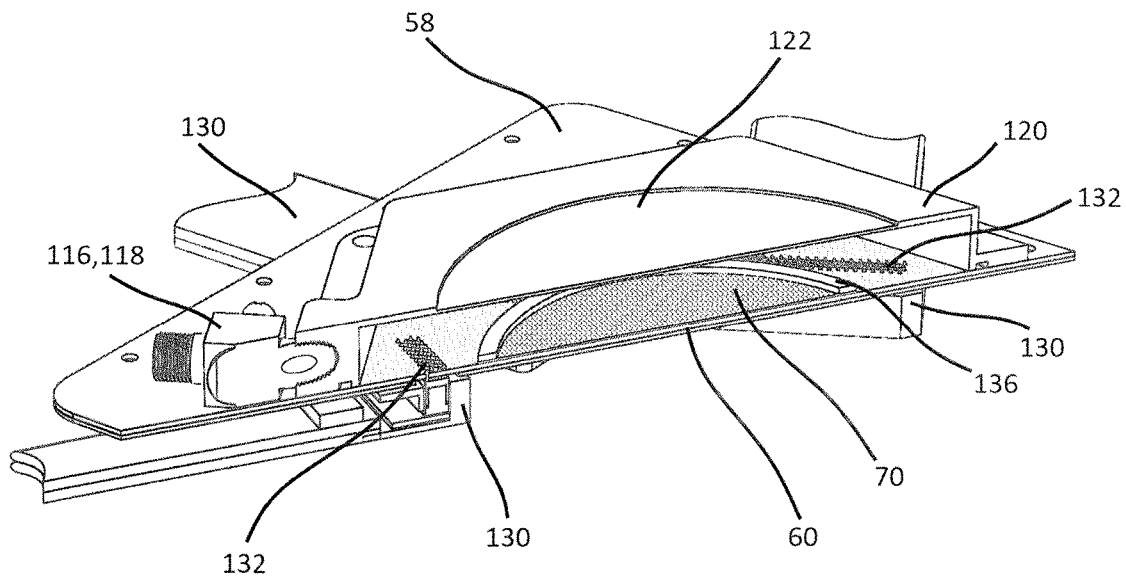

FIG. 5C shows a cross-sectional perspective view of the detector device 110 shown in FIGS. 5A and 5B, the cross-section being taken in a transverse plane. The array PCB 58 with the collector pads array area is covered by a gas volume cover 120 with a recessed beam entrance window 122. Inside the hermetic gas volume 112, the micromesh 70 is stretched across the circular frame 136 and rests parallel to the array PCB board 58 above the collector pads 50, 56 area, separated by the dielectric lattice 60. A number of high-density, through-hole mounted connectors 132 (such as, without limitation 6), and a number of data-bias-ground cables 130 (such as, without limitation 6) may supply detector grounds to the collector pads, transport the received ionization signals from each of the coordinate strips 54 through respective dedicated channels of the ZAP board and into the electronic data acquisition channel for each coordinate readout strip.

Figure 5D:
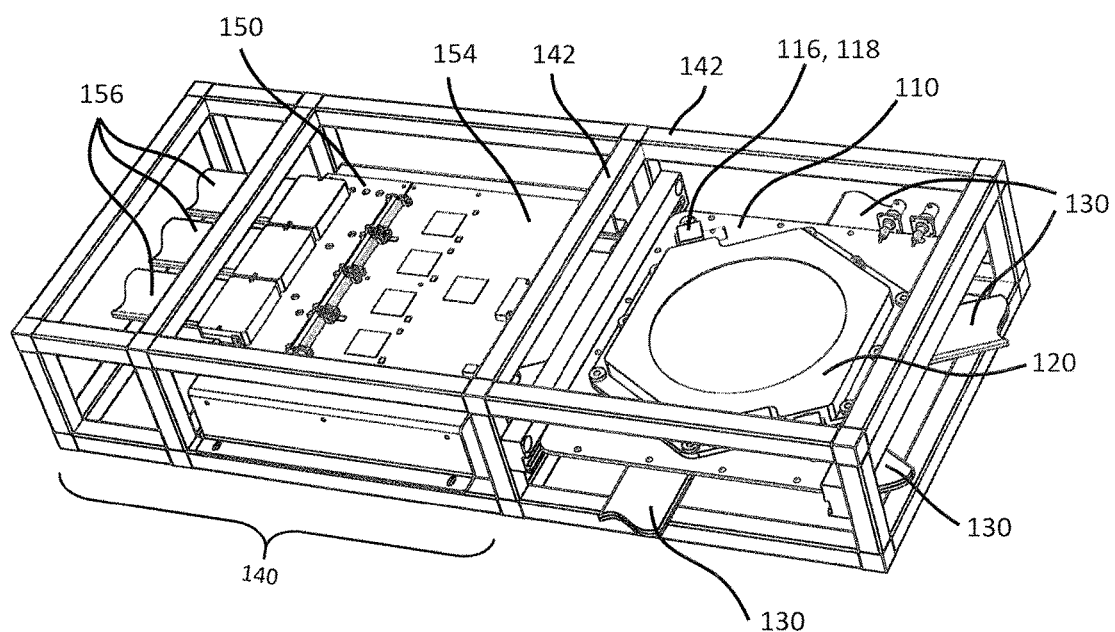

FIG. 5D, shows a perspective view of the detector device 110 together with readout electronics 140 in a frame body 142. The Micromegas based fluence and position detector device PCB array 110 that is covered and sealed with working gas by a machined cover 120, ZAP signal, bias, and protection/coupling board 150, joined together with the data acquisition electronics 154 are all housed within a tubular spatial frame 142. The detector device 110 may send the collected ionization signals, and receives the reference grounds to the collector pads 56, through a number of custom made cables 156, such as six.

Figure 6:
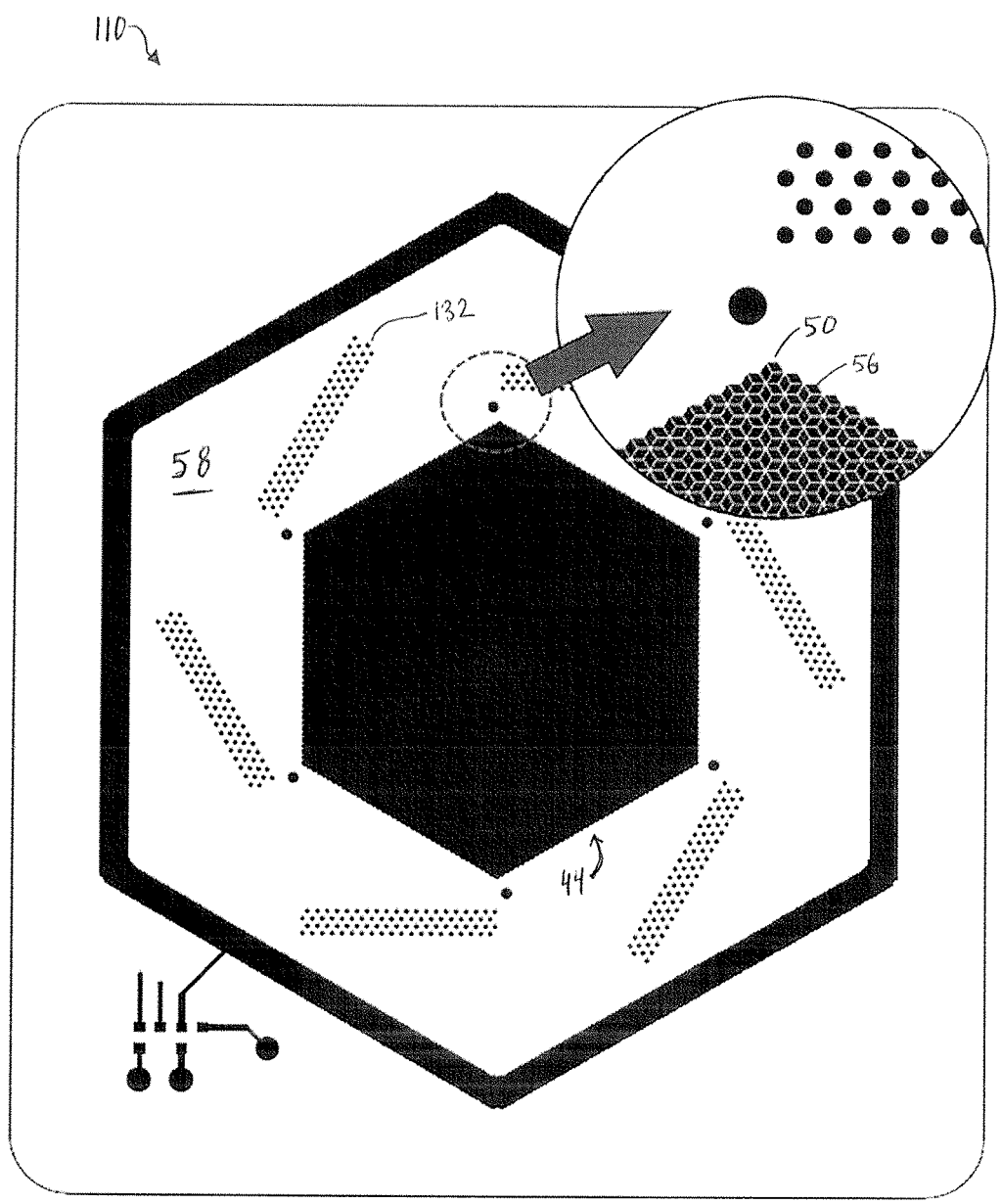
FIG. 6 shows a plan view of an embodiment of a detector array.

FIG. 6 shows a plan view of a conductive layer, such as a top copper layer of the PCB 58, for the Array 110. A top corner of the hexagonal Array is also shown in an enlarged view, so that the pad clusters 50 within the hexagonally shaped array are visible. The conductive lines, trace, or RDLs of the array 44 may extend from the clustered pads 50 and vias 52 in the hexagonal array to the ZAP connecters 152.

The PCB layout shown in FIG. 6 can include arrangements, adaptations, or configurations in which the anode pitch is on the order of 1 mm, or 0.1-10 mm. In some instances, common surface mount resistors can be incorporated on the anode circuit board. Alternatively, the resistor can be placed after the anode, not the resistive strip, for an improved arrangement.

By forming or arranging the Array as shown or described herein, the Array 44 is able to provide true sub-millimeter position accuracy. Accuracy can be obtained while keeping the overall number of readout channels relatively low, and on the order of about 200-300 connections, such as about 246 readout channel and can be the functional equivalent of 6724 readout electronic channels in the case where each pad is to be read out individually. As such, Applicant's Array and Device can obtain accurate beam exit position information while reducing or keeping number of readout channels count low and remaining within the dynamic range of the front-end acquisition electronics. Limiting a number of readout channels while increasing accuracy can be valuable for situations or arrangement using heavy isotope beams and data acquisition becomes an issue, such as when a cost of electronics per channel becomes prohibitively high in conventional per-pad data acquisition arrays. Similarly, use of 3D readouts for the array can manage or help manage signal rates and reduce or alleviate many of the data or pileup problems currently encountered.

Figure 7A:
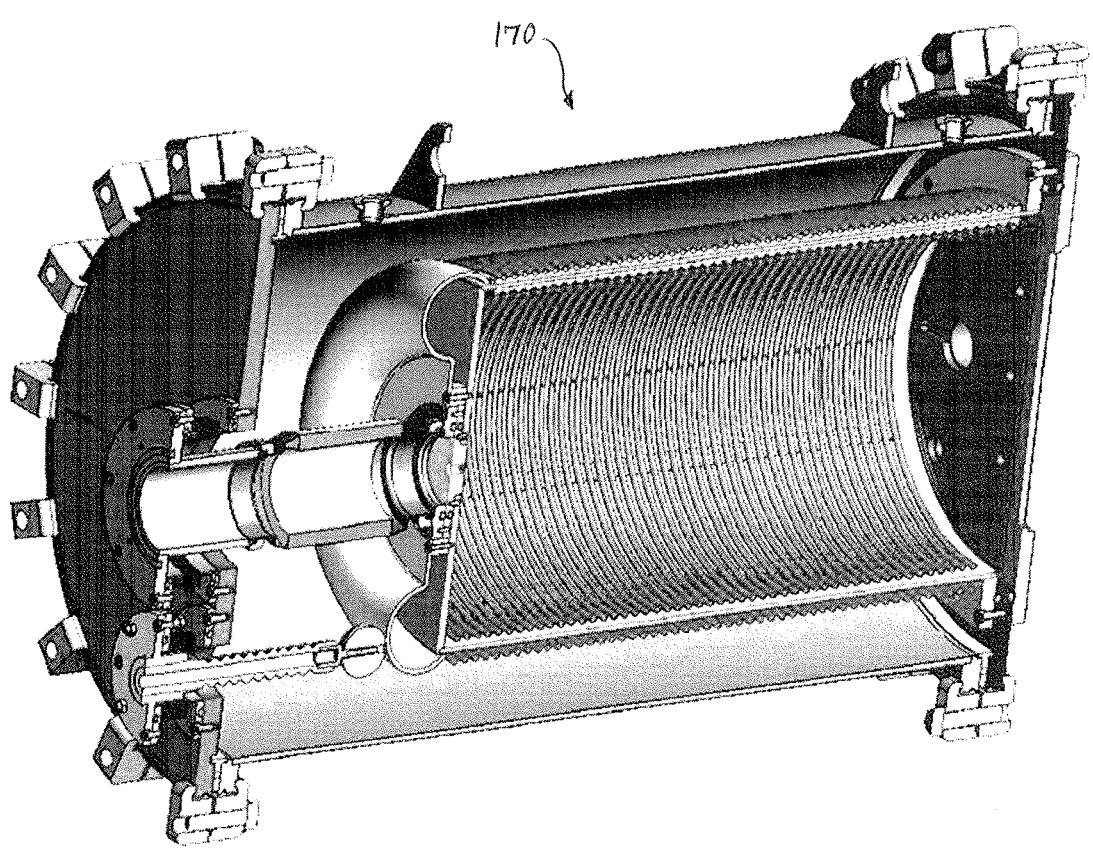
FIGS. 7A and 7B show perspective views of exemplary housings for detector arrays.
Figure 7B:
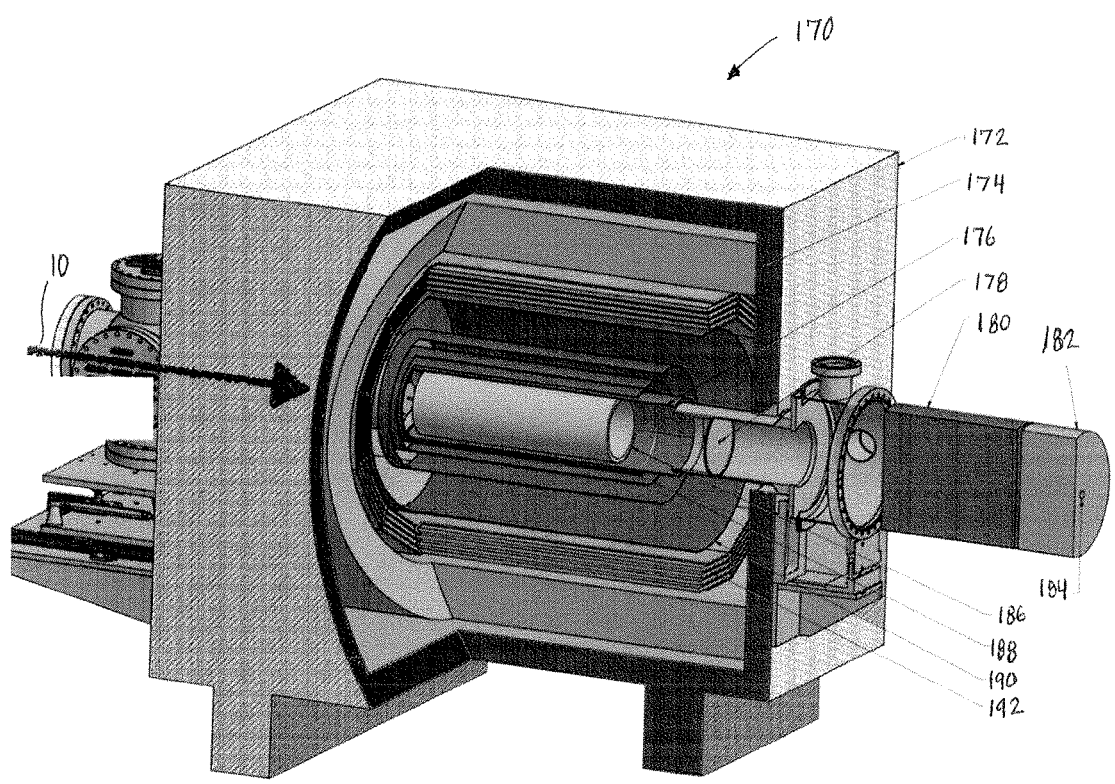

FIGS. 7A and 7B, show exemplary embodiments of chambers or housings 170 in which the Arrays and devices shown above can be housed and operate. FIG. 7A shows a PAT-TPC (prototype active target time projection chamber at NSCL laboratory, MI). FIG. 7B shows a concept of a Dark Light research detector that could potentially include Applicant's Micromegas arrays as one of the sub-detector systems.

FIG. 7B shows the chamber or housing 170 can comprise a magnet yoke 172, a magnet coil 174, a Be beam pipe 176, a downstream target limiter 178, a carbon moller dump 180, an iron moller dump 182, a beam exit 184, a proton detector 186, a lepton tracker 188, a lepton tracker 190, and a photon detector 192.

Applicant's Array can include superior mechanical stability and radiation damage resilience, as well as a high dynamic range and precision of radiation dose measurement with respect to conventional wire devices, and furthermore can significantly lower cost per channel with respect to conventional Micromegas systems and devices. As such, Applicant's Array can be used for measurement of intense proton/heavy ion beam fluence, position tracking, and cross section shape. The Array can also be used in either a 'direct detection' charge integration mode or a proportional gain mode with two distinct biasing schemes (pads biased or grounded). The Array can additionally be used as a conventional Micromegas array with very high resolution and low cost, which can be advantageously used in applications in nuclear and particle physics experiments.

In some embodiments, the Array can comprise an active area of at least 10 cm$^2$, spatial (X-Y) resolution of 1 mm or better, and can sample proton beam flux of $10^6$-$10^{13}$ particles/cm$^2$/second (s). As such Applicant's Array is useful in the fields of basic nuclear and particle physics instrumentation, experimental nuclear physics instrumentation, applied medical physics, medical devices in radiation oncology, industrial nuclear applications, and general industrial use, while retaining important performance traits of a high-precision scientific instrument that can additionally include application to general experimentalists in nuclear and particle research.

Applicant's Array can comprise a three-directional readout coordinate plane, high spatial resolution with a lower cost-per-channel than conventional devices (e.g. Micromegas), and can include an innovative symmetric split micro-pattern array design. The array can also comprise a gas-filled ionizing radiation detection with desirable resolution in three spatial dimensions (3D spatial). As such, the Array or versions thereof can be scalably built to include particle detector arrays that are large, clinically relevant, or both (including, e.g., area detector arrays of about 40 cm×40 cm, 50 cm×50 cm (plus or minus 0-20%, 0-10%, or 0-5%). Array size can be limited not by the scalability of Applicant's improvements, but by mesh tension and mechanical stability, as well as signal readout paths capacitance which becomes larger for high resolution of signals.

The Array or versions thereof can be scalably built to include particle detector arrays that are cost-effective, stable, comprise high spatial resolution (e.g. clinically relevant spatial resolutions per current radiation oncology of 1 mm, as well as improved resolutions in ranges of 1 mm-250 μm) and 1 mm-150 μm. In some instances, particle detector arrays can improve spatial resolution by the use of shared signal fractions among neighboring pads or pad clusters.

Applicant's Array can also provide improved radiation therapy, such as for cancer patients. In clinical practice, radiotherapy techniques use both accelerated photon or electron beam, as well as hadrons and/or heavy ions. The use of hadrons and/or heavy ions can be advantageous due to particular energy loss patterns for these heavy particles in tissue. Hadron treatment provides a straight path of hadrons with relatively low energy loss (and the respective dose deposition along the path) until the end of the trajectory where most energy loss occurs very rapidly in a small region is called Bragg peak. A depth of the Bragg peak can be controlled by modulation of proton energy during beam delivery, thus ensuring very high degree of dose conformity with almost no exit dose into healthy tissue, which, unlike photon therapy, delivers an undesired exit doses to healthy tissue.

Applicant's Array 44, 110 can advance radiation therapy by providing high spatial and time resolution accompanied by good linearity and very wide dynamic range in the Bragg peak position measurement by delivering conformity of transverse beam position (in X-Y) and fluence (intensity) profile with the proposed fluence detector followed with a multi-plate ionization chamber. Applicant's Array 110 110 can also advance radiation therapy by providing precision energy modulation of a proton beam as a universal 3-D dose and fluence instrument for quality assurance (QA) of therapeutic heavy ionizing particle beams.

To ensure that all of the detector array strips respond uniformly and register incoming radiation flux similarly in all three coordinates and across the entire active detection area of the array, a procedure of calibration must be performed. Such calibration procedure would include the adjustment of both the respective gain values for all readout channels in the data acquisition electronics, and assigning additional proportionality factors (calibration coefficients) in the data acquisition software, so that all channels would be producing similar response to the same amount of incoming radiation that they are being exposed to, while minimizing such response variations in all of the detector array channels.

Detector calibration procedure assumes that a radiation source device produces a certain fluence map that is while unknown, however is stable and does not change within localized intervals of time (on the order of several seconds) if there are no adjustments made to the radiation generation device (i.e. accelerator).

Detector calibration procedure assumes that a radiation source can produce a certain fluence map repeatedly multiple number of times, long as there are no adjustments made to the radiation generation device (i.e. the accelerator).

Detector calibration procedure assumes that the ionizing particle position and fluence detector array device can be re-positioned with respect to the generated radiation beam in a repeatable and reliable manner, i.e. could be rotated with respect to the beam center axis and/or shifted in directions perpendicular to the beam axis.

An iterative algorithm and method is devised to calibrate radiation response sensitivities of all array's registration channels. The detector array is irradiated with a wide, open-field radiation beam at the central position, with subsequently irradiated with the same wide radiation beam at laterally and longitudinal shifted positions. The unknown radiation beam fluence profile of the wide field is being reconstructed as series of iterations from the ratios of shifted images to the central image, solving a system of linear equations for the unknown calibration coefficients as minimization problem with respect to the differences in channel responses at corresponding locations in the radiation beam. The propagation errors due to possible radiation generator output variation and minor inaccuracies in array positioning are estimated and compensated for in the reconstructed initial beam profile by series of additional narrow open-field irradiations. The beam profile is interpolated when necessary if a precise location for certain detector pads is impossible to unambiguously correspond after each of the shifts and/or rotations, and then compared to raw detector responses to determine individual adjustments (calibration coefficients) to sensitivities for each of array's channels. These adjustments are then applied as correction factors in the data acquisition software, and array is calibrated.

While this disclosure includes a number of embodiments in different forms, the drawings and written descriptions herein with respect to the particular embodiments herein are presented with the understanding that the present disclosure is to be considered as an exemplification of the principles of the disclosed methods and systems, and is not intended to limit the broad aspect of the disclosed concepts to the embodiments illustrated. Additionally, it should be understood by those of ordinary skill in the art that other manufacturing devices and examples could be intermixed or substituted with those provided. In places where the description refers to particular embodiments, it should be readily apparent that a number of modifications may be made without departing from the spirit thereof and that these embodiments and implementations may be applied to other technologies as well. Accordingly, the disclosed subject matter is intended to embrace all such alterations, modifications and variations that fall within the spirit and scope of the disclosure and the knowledge of one of ordinary skill in the art.

What is claimed is:

1. A particle beam detector system, comprising:
a particle beam generator;
a Micromegas particle beam fluence and position detector array comprising:
  a sealed, gas-filled, ionizing radiation detector chamber,
  a printed circuit board (PCB) disposed within the ionizing radiation detector chamber, the PCB comprising a multi-layer array arrangement of interconnected conductive sensor pads with the conductive sensor pads disposed on the PCB and coupled to an interconnected series of corresponding strips comprising three planar coordinate grids, X, Y, and ST (stereo), the interconnected series of corresponding strips being situated as separate layers within the PCB, the arrangement of interconnected conductive sensor pads comprising a first footprint,
  wherein the interconnected conductive sensor pads form a plurality of interlocking three-coordinate detection clusters with each three-coordinate detection cluster coupled to the three planar coordinate grids, X, Y, and ST, such that the plurality of three-coordinate detection clusters extend across the PCB in a repeating pattern,
  a dielectric lattice structure, disposed over the PCB and extending away from the multi-layer array arrangement of sensors, and
  a conductive mesh structure comprising a second footprint disposed over the dielectric lattice structure and the PCB, the second footprint extending over an entire area of the first footprint;
electronic signal acquisition channels coupled to each of the conductive sensor pads and corresponding strips of the particle beam fluence and position detector array; and
data readout electronics coupled to the electronic signal acquisition channels.

2. The particle beam detector system of claim 1, wherein the plurality of interlocking three-coordinate detection clusters comprise a diamond shape X coordinate sensor, a diamond shape Y coordinate sensor, and a diamond shape ST coordinate sensor joined to form the interlocking three-coordinate detection clusters comprising a hexagonal shape.

3. The particle beam detector system of claim 1, wherein the dielectric lattice structure comprises openings of any shape through which a particle beam may pass to the multi-layer array arrangement of sensors.

4. The particle beam detector system of claim 1, wherein the electronic signal acquisition channels connected to each of the corresponding strips of the particle beam fluence and position detector array for resolving incoming flux intensity variations comprises fewer electronic signal acquisition channels than a second number of electronic signal acquisition channels using individual independent collector pads, wherein the second number of independent collector channels increases by a power law.

5. The particle beam detector system of claim 1, wherein the detector array comprises a curved surface to produce a cylindrical detector.

6. The particle beam detector system of claim 1, wherein the dielectric lattice structure comprises a wall thickness in a range of 0.003-0.5 millimeters (mm) and a height in a range of 50-300 micrometers (µm).

7. The particle beam detector system of claim 1, wherein:
the particle beam generator is adapted to send an ionizing particle beam to the detector array; and
the position detector array is oriented substantially perpendicular to a direction of a beam produced by the particle beam generator.

8. The particle beam detector system of claim 1, wherein the position detector array comprises a planar surface.

9. A particle beam detector array, comprising:
a sealed, gas-filled, ionizing radiation detector chamber;
a substrate disposed within the ionizing radiation detector chamber, the substrate comprising a multi-layer array arrangement of interconnected conductive sensor pads coupled to an interconnected series of corresponding strips comprising three planar coordinates X, Y, and ST (stereo), the sensor pads situated on the substrate, and the interconnected series of corresponding strips situated on three separate layers of the substrate;
wherein the interconnected conductive sensor pads form a plurality of interlocking three-coordinate detection clusters with each three-coordinate detection cluster coupled to the three planar coordinate grids, X, Y, and ST, such that the plurality of three-coordinate detection clusters extend across the PCB in a repeating pattern,
a dielectric lattice structure, disposed over the substrate and the plurality of interlocking three-coordinate detection clusters; and
a conductive mesh structure disposed over the dielectric lattice structure.

10. The particle beam detector array of claim 9, wherein the particle beam detector array comprises a Micromegas particle beam fluence and position detector array.

11. The particle beam detector array of claim 9, wherein the plurality of interlocking three-coordinate detection clusters comprise a a diamond shape X coordinate sensor, a diamond shape Y coordinate sensor, and a diamond shape ST coordinate sensor join to form a hexagonal shape.

12. The particle beam detector array of claim 9, wherein the dielectric lattice structure comprises openings of any shape through which a particle beam may pass to the multi-layer array arrangement.

13. The particle beam detector array of claim 9, wherein a first number of electronic signal acquisition channels for resolving incoming flux intensity variations is lower than a second number of electronic signal acquisition channels using individual independent collector pads for which the second number of independent collector channels increases by a power law.

14. The particle beam detector array of claim 9, wherein the multi-layer array arrangement comprises a curved surface to produce a cylindrical detector.

15. The particle beam detector array of claim 9, wherein the dielectric lattice structure comprises a wall thickness in a range of 0.003-0.5 millimeters (mm) and a height in a range of 50-300 micrometers (µm).

16. A method of using an ionizing particle beam detector system, comprising:

directing an ionizing particle beam from a particle beam generator to a particle beam fluence and position detector array, wherein the ionizing beam is directed in a direction substantially perpendicular to the position detector array;

measuring the ionizing particle beam fluence and position with a particle beam fluence and position detector array, the particle beam fluence and position detector array comprising interconnected conductive sensor pads that form a plurality of interlocking three-coordinate detection clusters; and calibrating the particle beam generator by adjusting particle beam generator to generate an ionizing particle beam comprising a fluence and position within one percent of a desired fluence and position.

17. The method of claim 16, further comprising:

the particle beam fluence and position detector array comprising a Micromegas particle beam fluence and position detector array; and directing the ionizing particle beam from the particle beam generator to a patient after uniquely calibrating the particle beam generator to radiate a tumor in the patient.

18. The method of claim 16, further comprising:

directing a first ionizing particle beam from the particle beam generator to a first position on the particle beam fluence and position detector array;

measuring a first an amount of radiation delivered by the first ionizing particle beam;

moving the particle beam generator;

directing a second ionizing particle beam from the particle beam generator to a second position on the particle beam fluence and position detector array;

measuring a second amount of radiation delivered by the second ionizing particle beam; and generating a planar map of fluence for the radiation delivered by the first ionizing particle beam and the second ionizing particle beam.

19. The method of claim 16, further comprising generating the ionizing particle beam as a heavy ionizing particle beam or a proton beam with a fluence on the order of $10^5$-$10^{14}$ ionizing particles per second.

20. The method of claim 16, further comprising resolving beam position and spot size to 0.8-1.2 mm, and measure of delivered dose radiation with an accuracy of less than or equal to 2% of a desired dose for beam monitoring of proton therapy.

21. The method of claim 16, wherein a particle beam fluence and position detector array comprise an active area greater than 10 centimeters squared ($cm^2$), a coordinate resolution (X, Y) less than 200 micrometers (μm) (Isotropic in X-Y), a beam flux dynamic range $10^6$-$10^{13}$ particles/$cm^2$/s±1%, a lifetime accumulated dose exposure greater than 50 kGy, a charge sensitivity less than 100 fC, and a response time less than 1 millisecond (ms).

* * * * *